United States Patent [19]

Kato et al.

[11] 4,390,406

[45] Jun. 28, 1983

[54] REPLACEABLE OUTER JUNCTION DOUBLE JUNCTION REFERENCE ELECTRODE

[75] Inventors: Kenneth J. Kato, Export; Dominick Frollini, Jr., Trafford, both of Pa.

[73] Assignee: Allied Corporation, Morris Township, Morris County, N.J.

[21] Appl. No.: 401,257

[22] Filed: Jul. 23, 1982

[51] Int. Cl.³ ............................................. G01N 27/26
[52] U.S. Cl. ...................................................... 204/435
[58] Field of Search ..................................... 204/195 F

[56] References Cited

U.S. PATENT DOCUMENTS

| | | | |
|---|---|---|---|
| 3,103,480 | 9/1963 | Watanabe | 204/195 F |
| 3,208,927 | 9/1965 | Arthur | 204/195 F |
| 3,423,304 | 1/1969 | Leonard | 204/195 F |
| 3,455,793 | 7/1969 | Watanabe | 204/195 F |
| 3,463,718 | 8/1969 | Detemple | 204/195 F |
| 3,530,056 | 9/1970 | Haddad | 204/195 F |
| 3,657,096 | 4/1972 | Proctor | 204/195 F |
| 4,282,081 | 8/1981 | Arrance | 204/195 F |

*Primary Examiner*—Arthur P. Demers
*Attorney, Agent, or Firm*—Webb, Burden, Robinson & Webb

[57] ABSTRACT

A double junction reference electrode which includes an inner body enclosing an inner chamber, a reference element disposed within and extending through the inner body, an outer body disposed around the inner body and enclosing an outer chamber between the inner body and the outer body, an inner ion path through the inner body and providing for the flow of ions between the inner and outer chambers, an outer ion path through the outer body and providing for the flow of ions between the outer chamber and the area exterior of the outer body, a means for introducing an electrolyte into the inner and outer chambers, and a means for releasably joining the inner and outer bodies together to form a unitary electrode structure.

10 Claims, 2 Drawing Figures

REPLACEABLE OUTER JUNCTION DOUBLE JUNCTION REFERENCE ELECTRODE

DESCRIPTION

1. Technical Field

This invention pertains to double junction reference electrodes and, more particularly, to double junction reference electrodes with a replaceable outer junction.

2. Background Art

As is well known in the art, a reference electrode is often utilized in a potentiometric measuring system, such as in pH measurement, titration, specific ion measurements, or the like. Typically a measuring electrode is inserted into a solution to be tested and measures the electrical potential between the solution and the measuring electrode resulting from some ionic property of the solution. A reference electrode is inserted into the solution and functions to provide a reference potential with respect to the solution which remains effectively at a constant, known value independent of variations in the solution under test. The reference electrode also functions to complete an electrical circuit from the potentiometric measuring apparatus, through the measuring electrode, solution under test, reference electrode, and back to the measuring apparatus. The potential difference between the reference and measuring electrodes is a function of the activity of certain ions in the solution. A common example is a conventional pH meter which uses a pair of electrodes adapted to measure the activity of hydrogen ions in a solution.

In one version, the reference electrode includes a reference element inserted into a plastic or glass body containing an electrolyte. Such an arrangement forms a half-cell which provides the constant reference potential needed for the measuring system. Ionic or electrical contact is maintained between the electrolyte and the test solution by way of a liquid junction through the body of the reference electrode. Examples of reference electrodes with a single junction are shown in U.S. Pat. Nos. 3,267,016; 3,282,818; 3,461,055; 3,463,718; 3,486,997; and 3,657,096; and British Pat. No. 678,648.

The most common types of reference electrodes utilize a reference element made from silver-silver chloride (Ag/AgCl) or mercury-mercurous chloride (calomel) and an electrolyte which is an aqueous solution of potassium chloride. Because of the presence of the liquid junction through the reference electrode body, the electrolyte may leak into and contaminate the solution under test. This is objectionable, for example, when measuring potassium or chloride ions and a potassium chloride electrolyte is used. Contamination of the test solution from heavy ions, such as mercurous ions from a calomel reference element, is objectionable when measuring certain biological media. In addition the liquid junction may become clogged from heavy metal precipitates.

To overcome this contamination problem from reference electrodes, double junction reference electrodes have been developed. See, for example, U.S. Pat. Nos. 3,103,480 and 3,455,793. In such electrodes, a standard reference electrode is surrounded by a second or outer glass or plastic body spaced from the reference electrode body, a non-contaminating electrolyte is placed in the space therebetween, and a second liquid junction is provided through the second body to complete the electrical circuit between the non-contaminating electrolyte and the solution under test. The non-contaminating electrolyte, typically a liquid containing a salt such as potassium nitrate or ammonium nitrate, effectively isolates the contamination of the reference element and surrounding electrolyte from the solution, without interferring with the normal operation of the reference electrode.

The particular non-contaminating electrolyte chosen will vary for different solutions and for the particular type of test being made. The required non-contaminating electrolyte is usually specified by the manufacturer of the measuring electrode. In addition, it may be necessary to change the second liquid junction to vary the liquid flow rate characteristics between the solution and the non-contaminating electrolyte. Furthermore, the non-contaminating electrolyte may itself become contaminated over a period of time.

In the double junction reference electrodes shown in U.S. Pat. Nos. 3,455,793 and 3,103,480, the second body is fixedly attached around the reference electrode. Thus, an entirely different and complete double junction reference electrode must be provided if it becomes necessary to use a different second liquid junction. While it might be possible to change the non-contaminating electrolyte via access opening 24 in U.S. Pat. No. 3,103,480 and via tube 24 in U.S. Pat. No. 3,455,793, such an operation is neither desirable nor practical.

U.S. Pat. No. 4,282,081 discloses a double junction reference electrode which may be disassembled for changing or refilling the electrolytes or for cleaning. However, this electrode includes quite a number of elements which must be threadedly assembled and disassembled and does not lend itself to rapid, easy changing of the electrolytes or liquid junctions used.

Therefore, it is an object of the present invention to provide a double junction reference electrode in which the second or outer body, with accompanying second liquid junction, may be easily and rapidly assembled or disassembled.

DISCLOSURE OF THE INVENTION

To overcome the problems with the prior art electrodes, we have invented a double junction reference electrode which includes an inner body enclosing an inner chamber, a reference element disposed within and extending through the inner body, an outer body disposed around the inner body and enclosing an outer chamber between the inner body and the outer body, an inner ion path through the inner body and providing for the flow of ions between the inner and outer chambers, an outer ion path through the outer body and providing for the flow of ions between the outer chamber and the area exterior of the outer body, a means for introducing an electrolyte into the inner and outer chambers, and a means for releasably joining the inner and outer bodies together to form a unitary electrode structure.

The inner body is preferably an elongated tube with a closed top and a closed bottom and the outer body is an elongated tube with an inner diameter larger than the outer diameter of the inner body and with an open top and a closed bottom. The inner and outer bodies are releasably joined together by an inner cap attached to the top of the inner body, an outer cap attached to the top of the outer body and an engagement element, preferably an elastomeric O-ring, located on the inner cap whereby the outer cap may be disposed around the inner cap and frictionally engage the O-ring to form a unitary electrode structure. The ion paths are preferably liquid junctions, such as ceramic junctions, which extend through the bottoms of the inner and outer bodies.

DETAILED DESCRIPTION OF THE DRAWINGS

Figure 1:
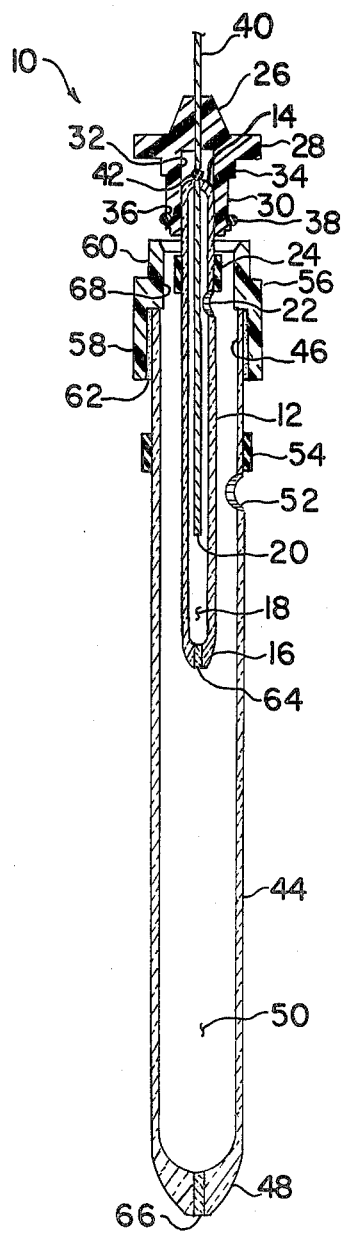
FIG. 1 is a longitudinal cross-sectional view of a double junction reference electrode in accordance with the present invention in the disassembled arrangement.
Figure 2:
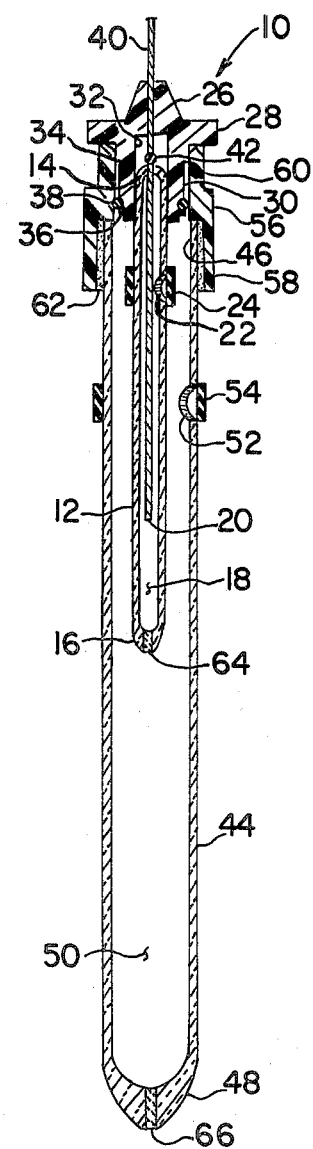
FIG. 2 is a longitudinal cross-sectional view of the double junction reference electrode of FIG. 1 in the assembled arrangement.

A double junction reference electrode in accordance with the present invention is shown in FIGS. 1 and 2. FIG. 1 shows the electrode 10 disassembled and FIG. 2 shows the electrode 10 assembled. Otherwise the elements of the electrode 10 shown in both figures are identical and will be identified by the same reference numerals.

The electrode 10 includes an elongated, tubular, preferably cylindrical, inner body 12, with a closed top 14 and a closed bottom 16, which encloses an inner chamber 18. A reference element 20 is disposed within the inner body and extends through the top 14. An inner access opening or port 22 extends through the side of the inner body 12 and forms a means for introducing an electrolyte into the inner chamber 18. An inner collar 24, made preferably of an elastomeric rubber, is slidingly positioned around the inner body 12 and may be moved to close off the inner port 22 after an electrolyte has been introduced into the inner chamber 18.

The electrode 10 includes an inner cap 26 which is secured to the top 14 of the inner body 12. The inner cap 26 includes a flange portion 28 and a narrower, integral neck portion 30 which extends downwardly from the flange portion 28. The top 14 of the inner body 12 is disposed within the inner cap 26 in a tubular aperture 32 which extends through the neck portion 30 and the inner body 12 is secured thereto by an adhesive or the like. The neck portion 30 also includes a raised ridge 34 at the area where the neck portion adjoins the flange 28. The inner cap 26 includes an integral groove 36 circumscribing the neck portion 30 and an engagement element, preferably an elastomeric silicone rubber O-ring 38, is positioned about the neck portion 30 in the groove 36. The O-ring 38 extends beyond the surface of the neck portion 30 slightly further than the thickness of the raised ridge 34.

An insulated electrical cable 40 passes through the inner cap 26 and is electrically connected to the reference element 20 by soldering, crimping or the like. Shown in the figures is a drop of solder 42 connecting the cable 40 and reference element 20 together. The cable 40 extends to and is connected to a potentiometer (not shown) or the like in the potentiometric measuring system.

The electrode 10 also includes an elongated, tubular, preferably cylindrical, outer body 44 with an open top 46 and a closed bottom 48 and with an inner diameter larger than the outer diameter of the inner body 12. When the electrode 10 is assembled, the outer body 44 is disposed around and spaced from the inner body 12 and encloses an outer chamber 50 therebetween. The inner body 12 is positioned within the outer body 44 through its open top 46. An outer access opening or port 52 extends through the side of the outer body 44 and forms a means for introducing an electrolyte into the outer chamber 50. An outer collar 54, made preferably of an elastomeric rubber, is slidingly positioned around the outer body 44 and may be moved to close off the outer port 52 after an electrolyte has been introduced into the outer chamber 50.

An outer cap 56 is attached to the top 46 of the outer body 44. The outer cap 56 includes a first tubular, cylindrical portion 58 integral with a second tubular, cylindrical portion 60 of a lesser diameter extending upwardly from the first portion 58. The outer body 44 is attached to the outer cap 56 within the first cylindrical portion 58 by an adhesive 62 or the like and the second cylindrical portion 60 extends above the top 46 of the outer body 44. The inner diameter of the second cylindrical portion 58 is slightly smaller than the outer diameter of O-ring 38 and approximately the same size as the outer diameter of the raised neck portion 30 of the inner cap 26.

The inner body 12 includes an inner ion path 64 which extends through the bottom 16 of the inner body and provides a path for the flow of ions between the inner chamber 18 and the outer chamber 50. The outer body 44 includes an outer ion path 66 which extends through the bottom 48 of the outer body and provides a path for the flow of ions between the outer chamber 50 and the area exterior of the outer body. Since, typically, liquid electrolytes are utilized in connection with the testing of liquid samples, a liquid junction will be the most commonly used ion path. Available liquid junctions which may be used, as is known in the art, include porous ceramic junctions, sleeve junctions, and cracked bead junctions. The particular junctions selected will be determined by the requirements of the potentiometeric measuring system within which the reference electrode is used.

The inner cap 26 and the outer cap 56, together with the O-ring 38, form a means for releasably joining the inner body 12 and the outer body 44 together to form a unitary double junction reference electrode structure. The inner chamber 18 of the inner body 12 is first filled with a suitable electrolyte through the inner port 22 and the inner port is sealed by moving the inner collar 24 over the inner port as shown in FIG. 2. Then the inner body 12 and inner cap 26 combination is inserted through the top 46 of the outer body 44 until the top of the second cylindrical portion 60 of the outer cap 56 abuts the flange portion 28 of the inner cap 26. In this manner, the O-ring frictionally engages the inner surface 68 of the second cylindrical portion 60 and holds the inner cap 26 and outer cap securely together, thereby forming a unitary electrode structure as shown in FIG. 2. The raised ridge 34 on the neck portion 30 of the inner cap 26 aids in joining the inner cap 26 to the outer cap 56 and provides a support for the upper end of the second cylindrical portion 60 adjacent the flange 28. A suitable electrolyte may be introduced into the outer chamber 50 through the outer port 52 and the inner port sealed off by the outer collar 54.

The outer body 44 may easily be removed by merely pulling downwardly to separate the outer cap 56 from the inner cap 26. In this manner, the electrolyte in the outer chamber 50 may be removed, the outer body 44 may be cleaned, or a different outer body, with either a different material construction or different outer ion path 66, may be substituted.

The inner body 12 and the outer body 44 may be constructed of glass or a polymer as is known in the art.

The inner cap 26 and the outer caps 56 are preferably made from an easily machinable polymer plastic. The reference element 20 may be the commonly used silver/silver chloride or mercury/mercurous chloride, also known as calomel, electrodes, or the like. The electrolyte in the inner chamber 18 is typically a potassium chloride solution, while the electrolyte in the outer chamber may be a liquid containing a salt, such as potassium nitrate or ammonium nitrate.

Having described the preferred embodiment of the present invention, it is to be understood that the invention may be otherwise embodied within the scope of the appended claims.

We claim:

1. A double junction reference electrode comprising:
   (a) an inner body enclosing an inner chamber wherein the inner body is an elongated tube with a closed top and a closed bottom;
   (b) a reference element disposed within and extending through the inner body;
   (c) an outer body disposed around the inner body and enclosing an outer chamber between the inner body and the outer body wherein the outer body is an elongated tube with an inner diameter larger than the outer diameter of the inner body and with an open top and a closed bottom;
   (d) an inner ion path through the inner body and providing for the flow of ions between the inner chamber and the outer chamber;
   (e) an outer ion path through the outer body and providing for the flow of ions between the outer chamber and the area exterior of the outer body;
   (f) means for introducing an electrolyte into the inner chamber and the outer chamber; and
   (g) means for releasably joining the inner body and outer body together which includes an inner cap attached to the top of the inner body, an outer cap attached to the top of the outer body, and an engagement element located on the inner cap whereby the outer cap may be disposed around the inner cap and frictionally engage the engagement element to form a unitary electrode structure.

2. The electrode of claim 1 wherein the engagement element includes an elastomeric O-ring secured to the inner cap.

3. The electrode of claim 1 wherein the reference element is an elongated silver/silver chloride electrode which extends through the top of the inner body.

4. The electrode of claim 1 wherein the reference element is an elongated calomel electrode which extends through the top of the inner body.

5. The electrode of claim 1 wherein the inner ion path is an inner liquid junction extending through the bottom of the inner body and the outer ion path is an outer liquid junction extending through the bottom of the outer body.

6. The electrode of claim 5 wherein the inner and outer liquid junctions are made of a ceramic material.

7. The electrode of claim 1 wherein the means for introducing an electrolyte into the inner chamber and outer chamber comprises an inner port extending through the inner body and an outer port extending through the outer body.

8. The electrode of claim 7 further includes a slidable inner collar secured about the inner body and a slidable outer collar secured about the outer body, wherein the inner collar and the outer collar may be moved to seal off the inner port and the outer port respectively.

9. The electrode of claim 1 further including an electrolyte in the inner chamber and the outer chamber.

10. The electrode of claim 9 wherein the electrolyte in the inner chamber is a potassium chloride solution.

* * * * *